United States Patent
Hickey et al.

(10) Patent No.: US 10,420,840 B2
(45) Date of Patent: Sep. 24, 2019

(54) ANTICANCER THERAPEUTIC AGENTS

(71) Applicant: RLL, LLC, Lutherville, MD (US)

(72) Inventors: Robert J. Hickey, Lakeview Terrace, CA (US); Linda H. Malkas, Lakeview Terrace, CA (US)

(73) Assignee: RLL, LLC, Lutherville, MD (US)

( * ) Notice: Subject to any disclaimer, the term of this patent is extended or adjusted under 35 U.S.C. 154(b) by 0 days.

(21) Appl. No.: 14/684,259

(22) Filed: Apr. 10, 2015

(65) Prior Publication Data

US 2016/0296482 A1    Oct. 13, 2016

(51) Int. Cl.
*A61K 45/06* (2006.01)
*A61K 31/167* (2006.01)
*A61P 35/00* (2006.01)

(52) U.S. Cl.
CPC ............ *A61K 45/06* (2013.01); *A61K 31/167* (2013.01); *A61P 35/00* (2018.01)

(58) Field of Classification Search
CPC .............................. A61K 31/167; A61K 45/06
USPC ......................................................... 514/616
See application file for complete search history.

(56) References Cited

U.S. PATENT DOCUMENTS

| | | | |
|---|---|---|---|
| 5,627,165 A | 5/1997 | Glazier | |
| 9,527,895 B2 * | 12/2016 | Hickey | .............. A61K 38/08 |
| 2005/0037090 A1 | 2/2005 | McKearn et al. | |
| 2008/0206140 A1 | 8/2008 | Hickey et al. | |
| 2009/0061432 A1 * | 3/2009 | Hoelz | ................ C07K 14/4738 435/6.14 |
| 2009/0123487 A1 | 5/2009 | Rothhaar | |
| 2011/0059953 A1 | 3/2011 | Boeckler et al. | |
| 2013/0345231 A1 * | 12/2013 | Hickey | ............... A61K 31/517 514/252.14 |
| 2015/0259407 A1 * | 9/2015 | Hickey | ............. C07K 16/3015 424/450 |

OTHER PUBLICATIONS

Pathalk et al., Enzymic protecting group techniques in organic synthesis, Stereosel. Biocatal. 775-797 (2000).
Remington: The Science and Practice of Pharmacy, (21st ed., 2005).
CellTitter Clo Assay https://www.promega.com/products/cell-health-and-metabolism/cell-viability-assays/celltiter_glo-luminescent-cell-viability-assay/.
L. Malkas et al., Biochemistry 29: 6362-6374 (1990).
Nam S., et al. "Dual inhibition of Janus and Src family kinases by novel indirubin derivative blocks constitutively-activated Stat3 signaling associated with apoptosis of human pancreatic cancer cells" Mol. Oncol. Jun. 2013;7(3):369-78. doi: 10.1016/j.molonc.2012.10.013 PMID: 23206899).
Metadynamics (Laio, A.; Parrinello, M. (2002). "Escaping free-energy minima". Proceedings of the National Academy of Sciences of the United States of America 99 (20): 12562-12566.
Pubchem-'409' Create Date: Jul. 30, 2006. p. 3, compound.
International Search Report issued in corresponding International Application No. PCT/US16/26619 dated Jul. 15, 2016.

* cited by examiner

*Primary Examiner* — Sabiha N Qazi
(74) *Attorney, Agent, or Firm* — Whiteford, Taylor & Preston, LLP; Peter J. Davis (57) ABSTRACT

The invention described herein pertains to anticancer therapeutic agents that exhibit preferential cytotoxicity to malignant cells that express a cancer specific isoform of proliferating cell nuclear antigen (caPCNA) compared to cytotoxicity to comparable non-malignant cells, pharmaceutical compositions comprising the agents, and their use in cancer therapy.

5 Claims, 8 Drawing Sheets

ANTICANCER THERAPEUTIC AGENTS

GOVERNMENT RIGHTS

This invention was made with government support in part under Grant No. W81XWH-07-1-0707 awarded by the Congressionally Directed Medical Research Programs (CD-MRP) Breast Cancer Research Program of the Department of Defense; Grant No. RO1 CA121289 awarded by the National Institutes of Health/National Cancer Institute; and a generous gift from the A.N.N.A. Foundation.

The U.S. government has certain rights in the invention.

TECHNICAL FIELD

The invention described herein pertains to anticancer therapeutic agents that exhibit preferential cytotoxicity to malignant cells that express a cancer specific isoform of proliferating cell nuclear antigen (caPCNA) compared to cytotoxicity to comparable non-malignant cells, pharmaceutical compositions comprising the agents, and their use in cancer therapy.

BACKGROUND

Proliferating cell nuclear antigen (PCNA) plays an important role in the process of DNA replication, repair, chromosomal recombination, cell cycle check-point control and other cellular proliferative activities. In conjunction with an adaptor protein, replication factor C (RFC), PCNA forms a moving clamp that is the docking point for DNA polymerases delta and epsilon. Different isoforms of proliferating cell nuclear antigen (PCNA) that display both acidic and basic isoelectric points (pI) have been demonstrated. Analysis of PCNA by two-dimensional polyacrylamide gel electrophoresis (2D PAGE) from both malignant and non-malignant breast cells (referred to as non-malignant PCNA or nmPCNA) and tissues revealed the presence of an acidic form of PCNA only in malignant cells (referred to as the cancer-specific PCNA or csPCNA or caPCNA, herein caPCNA). This difference in isoelectric point between these two forms of PCNA appears to result from an alteration in the ability of the malignant cells to post-translationally modify the PCNA polypeptide and is not due to a genetic change within the PCNA gene.

It has been shown that antibodies or peptides which bind only to the caPCNA isoform and not to the nmPCNA isoform interfere with intracellular protein-protein interactions, thereby causing a reduction in the proliferative potential of cancer. See, for example, WO 2006/116631 and WO 2007 098/415.

Also, PCNA is also known to interact with other factors like FEN-1, DNA ligase, and DNA methyl transferase. Additionally, PCNA was also shown to be an essential player in multiple DNA repair pathways. Interactions with proteins like the mismatch recognition protein, MSH2, and the nucleotide excision repair endonuclease, XPG, have implicated PCNA in processes distinct from DNA synthesis. Interactions with multiple partners generally rely on mechanisms that enable PCNA to selectively interact in an ordered and energetically favorable way.

SUMMARY OF THE INVENTION

The present invention arises from the discovery of small molecule therapeutic agents which exhibit preferential cytotoxicity to malignant cells that express the cancer specific isoform of proliferating cell nuclear antigen (caPCNA) compared to cytotoxicity to comparable non-malignant cells, see, e.g., U.S. Publication Number 2013/0345231 (incorporated herein by reference in its entirety). Without being bound by theory and as described below, it is believed these small molecule therapeutic agents exert their action through specific binding modes which inhibit protein-protein interactions involving caPCNA. Once docked with caPCNA, these molecules either reduce or prevent caPCNA from interacting with its natural set of binding partners. This disruption in binding partner interaction results in inhibition of specific cellular functions requiring both caPCNA and its binding partner (e.g., DNA replication and DNA repair). See, for example, FIG. 1.

Thus, small molecules bound to the protein-protein interaction domain of caPCNA or its binding partners (including, but not limited to, DNA polymerase δ, Xeroderma Pigmentosum G protein (XPG), or Flap-endonuclease (FEN-1)), would in-turn reduce/eliminate the ability of a cancer cell to properly replicate and/or repair its DNA; leading to the killing of the cancer cell. Also, the small molecule inhibitors of caPCNA-mediated function might have better therapeutic efficacy than the caPCNA derived octapeptides described above, because of the intrinsic stability properties of these specific small molecules within the blood-stream and tissues, relative to the stability of the peptides, and the issue of selectively directing sufficient quantities of the peptide into cancer cells without having the bulk of the peptide being taken up by cells in the blood-stream or surrounding tissues.

In one illustrative embodiment of the invention, a method of reducing cellular proliferation of malignant cells that express a cancer specific isoform of proliferating cell nuclear antigen (caPCNA) in a patient in need thereof, comprising administering a therapeutically effective amount of a compound of the formula, (hereinafter designated AOH39), or a substituted derivative thereof, or a pharmaceutically acceptable salt thereof, is described herein.

In another embodiment, there is described the use of a compound as described above or a substituted derivative thereof, or a pharmaceutically acceptable salt thereof, for reducing cellular proliferation of malignant cells that express a cancer specific isoform of proliferating cell nuclear antigen (caPCNA).

In another embodiment, there is described a pharmaceutical composition comprising a compound as described above or a substituted derivative thereof, or a pharmaceutically acceptable salt thereof, and further comprising one or more carriers, diluents, or excipients, or a combination thereof.

It is appreciated herein that the compounds described herein may be used alone or in combination with other compounds useful for treating cancer, including those compounds that may be therapeutically effective by the same or different modes of action.

DETAILED DESCRIPTION

According to the invention, small molecule therapeutic agents exert their action through specific binding modes which inhibit protein-protein interactions involving caPCNA. Once docked with caPCNA, these molecules either reduce or prevent caPCNA from interacting with its natural set of binding partners. This disruption in binding partner interaction results in inhibition of specific cellular functions requiring both caPCNA and its binding partner (e.g., DNA replication and DNA repair).

Figure 1:
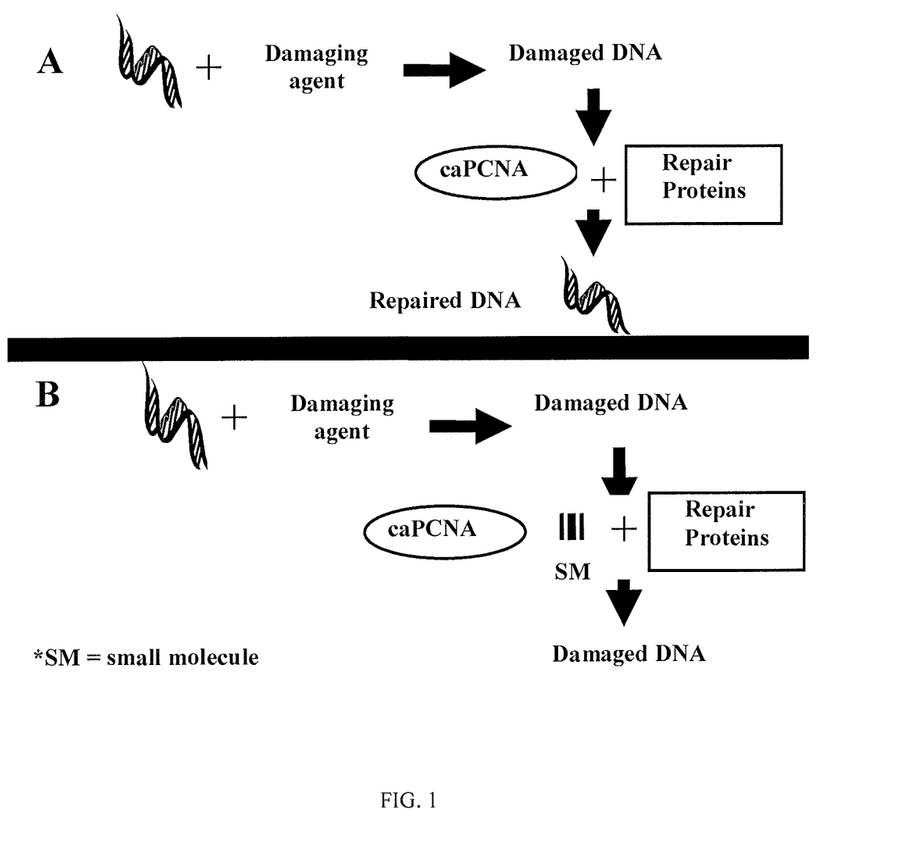
FIG. 1 shows a proposed Scheme for caPCNA action.

FIG. 1 shows a proposed Scheme for caPCNA action according to a theory behind the invention. Panel A represents how doxorubicin (DOX) induced DNA damage is normally repaired in cancer cells. caPCNA would interact with DNA repair proteins to facilitate fixing the damaged DNA. Panel B represents the conditions when the small molecule therapeutic agent (SM) is present in a cell that has DOX induced DNA damage. In this case the small molecule therapeutic agent (SM) binding with caPCNA or its binding partner competes with the full length caPCNA protein binding to its DNA repair protein partners, thereby, preventing the repair of the damaged DNA.

Embodiments of the invention are further described by the following enumerated clauses:

1. A method of reducing cellular proliferation of malignant cells that express a cancer specific isoform of proliferating cell nuclear antigen (caPCNA) in a patient in need thereof, comprising administering a therapeutically effective amount of a compound of the formula or a substituted derivative thereof, or a pharmaceutically acceptable salt thereof.

2. Use of a compound as described in clause 1 or a substituted derivative thereof, or a pharmaceutically acceptable salt thereof, for reducing cellular proliferation of malignant cells that express a cancer specific isoform of proliferating cell nuclear antigen (caPCNA).

3. A pharmaceutical composition comprising a compound as described in clause 1 or a substituted derivative thereof, or a pharmaceutically acceptable salt thereof, and further comprising one or more carriers, diluents, or excipients, or a combination thereof.

4. The method, use or composition of any of clauses 1-3 or a substituted derivative thereof, or a pharmaceutically acceptable salt thereof.

5. The method, use or composition of any of clauses 1-4 wherein the cancer is breast cancer.

6. The method, use or composition of any of clauses 1-4 wherein the cancer is pancreatic cancer.

7. The method, use or composition of any of clauses 1-4 wherein the cancer is neuroblastoma.

8. The method or use of any of clauses 1-7 wherein the use is to augment another chemotherapeutic method.

9. A pharmaceutical composition comprising a compound as described in clause 3 and a further chemotherapeutic agent.

As used herein, a substituted derivative of an illustrated compound includes one in which one or more hydrogens has been replaced by, for example, a halo, hydroxy and derivatives thereof, amino and derivatives thereof, thio and derivatives thereof, acyl, alkyl, alkenyl, alkynyl, cycloalkyl, aryl, arylalkyl, heteroalkyl, cycloheteroalkyl, heteroaryl, heteroarylalkyl, alkylsulfinyl, alkylsulfonyl, arylsulfinyl, arylsulfonyl, heteroarylsulfinyl or heteroarylsulfonyl group, each of which may bear one or more substituents, as well as a derivative in which, for example one or more halo, hydroxy or alkyl groups has been replaced by a hydrogen.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives include, but are not limited to, both those compounds that may be synthetically prepared from the compounds described herein, as well as those compounds that may be prepared in a similar way as those described herein, but differing in the selection of starting materials. For example, described herein are compounds that include aromatic rings. It is to be understood that derivatives of those compounds also include the compounds having for example different substituents on those aromatic rings than those explicitly set forth in the definition above. In addition, it is to be understood that derivatives of those compounds also include the compounds having those same or different functional groups at different positions on the aromatic ring. Similarly, derivatives include variations of other substituents on the compounds described herein, such as on an alkyl group or an amino group, and the like.

It is to be understood that such derivatives may include prodrugs of the compounds described herein, compounds described herein that include one or more protection or protecting groups, including compounds that are used in the preparation of other compounds described herein.

It is to be understood that such derivatives may be mixed with other compounds that improve the stability and biological distribution of the compounds described here in.

Illustrative derivatives include, but are not limited to, those compounds that share functional and in some cases structural similarity to those compounds described herein. For example, described herein are compounds that include a ring system. Illustrative substituted derivatives include, but are not limited to, the corresponding ring expanded compounds, and the corresponding ring systems that include one or more heteroatoms, such as by substitution of a methylene group with an oxa, thia or optionally substituted amino group, or substitution of an aromatic C—H group with an N.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000) (incorporated herein by reference in their entirety). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "patient" includes both human and non-human patients, such as mammals, including companion animals and other animals in captivity, such as zoo animals.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

In addition, in those embodiments described herein drawn to combination therapy comprising administration of a chemotherapeutic agent and a small molecule therapeutic agent of the instant invention, "therapeutically effective amount" refers to that amount of the combination of agents taken together so that the combined effect elicits the desired biological or medicinal response. For example, the therapeutically effective amount of doxorubicin and a small molecule therapeutic agent of the instant invention, would be the amounts that when taken together or sequentially have a combined effect that is therapeutically effective. Further, it is appreciated that in some embodiments of such methods that include coadministration, that coadministration amount of the chemotherapeutic agent or the small molecule therapeutic agent of the instant invention when taken individually may or may not be therapeutically effective.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol, DMSO, Cremophor, etc., can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

Depending upon the disease as described herein, and the route of administration, a wide range of permissible dosages are contemplated herein, including doses falling in the range from about 1 µg/kg to about 1 g/kg. The dosages may be single or divided, and may be administered according to a wide variety of protocols, including q.d., b.i.d., t.i.d., or even every other day, once a week, once a month, once a quarter, and the like. In each of these cases it is understood that the total daily, weekly, month, or quarterly dose corresponds to the therapeutically effective amounts described herein. When given locally, such as by injection near or at the site of disease, illustrative doses include those in the range from about 1 µg/kg to about 10 mg/kg, or about 0.01 mg/kg to about 10 mg/kg, or about 0.01 mg/kg to about 1 mg/kg, or about 0.1 mg/kg to about 10 mg/kg, or about 0.1 mg/kg to about 1 mg/kg. When given locally, such as by injection near the site of disease, or locally in tissues surrounding the site of disease, illustrative doses include those in the range from about 0.01 mg/kg to about 10 mg/kg, or about 0.01 mg/kg to about 1 mg/kg, or about 0.1 mg/kg to about 10 mg/kg, or about 0.1 mg/kg to about 1 mg/kg. When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg. When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In another illustrative embodiment, such as when treating a disease described herein, the compound is administered parenterally locally q.d. at a dose of about 0.01 mg/kg, or about 0.05 mg/kg, or about 0.1 mg/kg, or about 0.5 mg/kg, or about 1 mg/kg, or about 5 mg/kg of body weight of the patient.

In another illustrative embodiment, such as when treating a systemic condition, the compound is administered parenterally systemically q.d. at a dose of about 0.1 mg/kg, or about 0.5 mg/kg, or about 1 mg/kg, or about 5 mg/kg, or about 10 mg/kg, or about 50 mg/kg of body weight of the patient.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The following examples further illustrate specific embodiments of the invention; however, the following illustrative examples should not be interpreted in any way to limit the invention.

EXAMPLES

Compounds exemplified herein, as denoted by "AOH" numbers were obtained or derived from compounds contained in screening chemical libraries used by AMRI (formerly Albany Medical Research, Inc.), Albany, N.Y. to identify AOH 39.

Other small molecule inhibitors of caPCNA-mediated function of the invention may be prepared by conventional synthetic routes.

Figure 2:
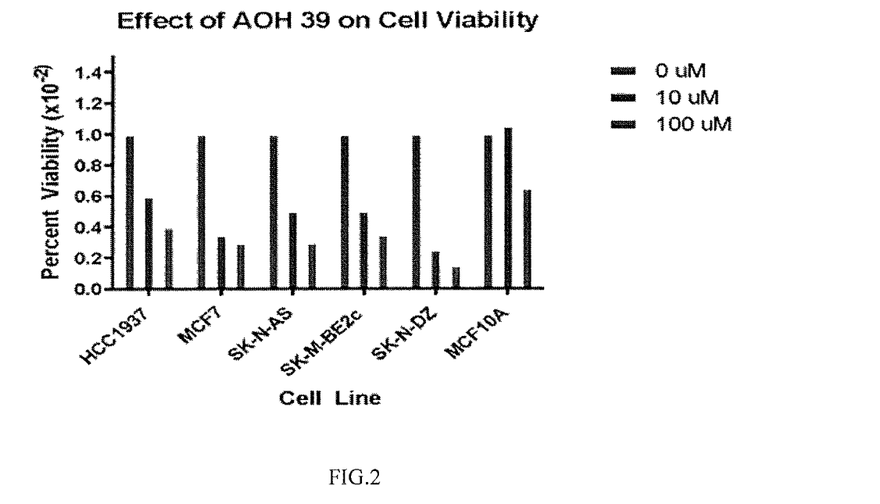
FIG. 2 shows the viability of breast cancer and Neuroblastoma cell lines incubated for 72 hours with the indicated concentrations of AOH39 or a phosphate buffered saline (PBS)/DMSO control lacking drug.

Effect of AOH39 on Cell Viability:

The effect of AOH39 on cell viability was studied by examining the viability of breast cancer and Neuroblastoma cell lines incubated for 72 hours with the indicated concentrations of AOH39 or a phosphate buffered saline (PBS)/DMSO control lacking drug. See FIG. 2.; HCC1937—is a BRCA1 defective breast cancer cell line; MCF7—is an ER+ Breast Cancer cell line; MCF10A is a non-malignant but immortalized breast cell line; SK-N-AS, SK-N-BE2c, and SK-N-DZ lines are neuroblastoma cell lines; The X-axis lists the various cell lines tested. The Y-Axis shows cell proliferation as a percentage of proliferation in cultures grown in the presence of PBS/DMSO without added AOH39. Proliferation was monitored using the CellTiter Glo Assay (Promega Inc., Madison, Wis.) (https://www.promega.com/products/cell-health-and-metabolism/cell-viability-assays/celltiter-glo-luminescent-cell-viability-assay/). The histogram was generated using Prism 6.

Inhibition of SV40 In Vitro DNA Replication by AOH39

Figure 3:
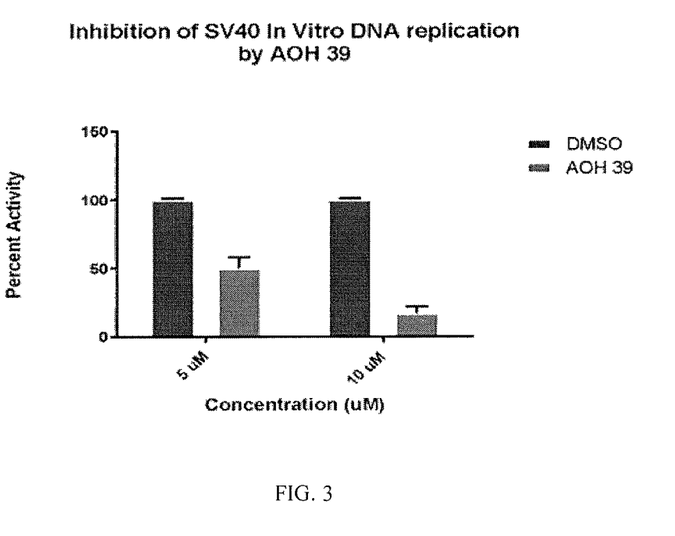
FIG. 3 shows inhibition of MCF7 Cell SV40 origin-dependent In Vitro DNA replication By AOH39.

In vitro DNA replication activity was determined using the standard T-antigen and SV40 origin dependent in vitro DNA replication reaction (L. Malkas et al., Biochemistry 29: 6362-6374 (1990) and percent inhibition was determined relative to a reaction containing Tris-HCl/DMSO in place of AOH39.) The reaction was started with the addition of T-antigen to the reaction mixture. Results are shown in FIG. 3, with AOH39 inhibiting replication by roughly 50% at concentrations of 5 µM and by more than 75% at 10 µM.

Correlation Between AOH39-Mediated MCF7 Cell Cytotoxicity and Inhibition of MCF7 Cell Extract-Mediated In Vitro DNA Replaction.

Figure 4:
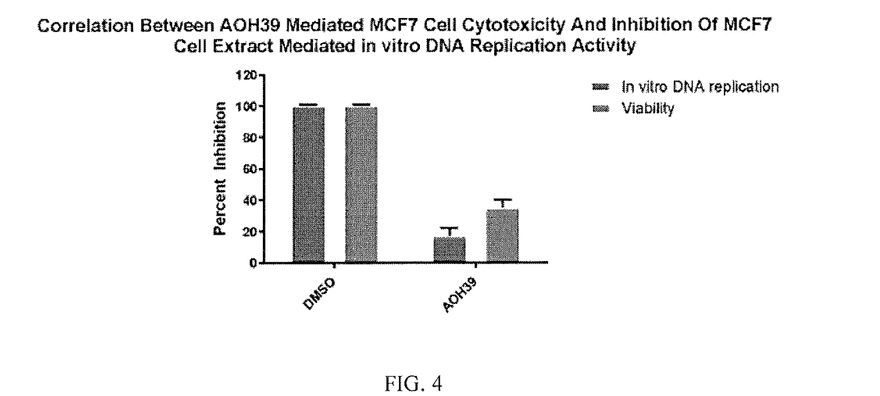
FIG. 4 shows correlation between AOH39-mediated cytotoxicity in MCF7 cells, and in vitro DNA replication activity mediated by the DNA synthesome isolated from these cells.

There is a precise correlation between the ability of AOH39 to inhibit the SV40 origin dependent in vitro DNA replication process and MCF7 cell viability, FIG. 4. Cell viability was determined colorimetrically using the MTT assay following a 72 hour incubation with 10 µM of AOH39. In vitro DNA replication activity was determined using the standard T-antigen and SV40 origin dependent in vitro DNA replication reaction (L. Malkas et al., Biochemistry, 29, 6362-6374 (1990)), and percent inhibition was determined relative to a reaction containing Tris-HCl/DMSO in place of AOH39 for the activity assay, and PBS/DMSO for the viability assay. AOH39 inhibited DNA replication significantly, relative to a control replication reaction containing PBS/DMSO in place of compound, and inhibition correlated precisely with a significant decrease in MCF7 cell viability.

Predicted Interaction of AOH 39 with the PIP Boxinteraction Domain of caPCNA.

Figure 5:
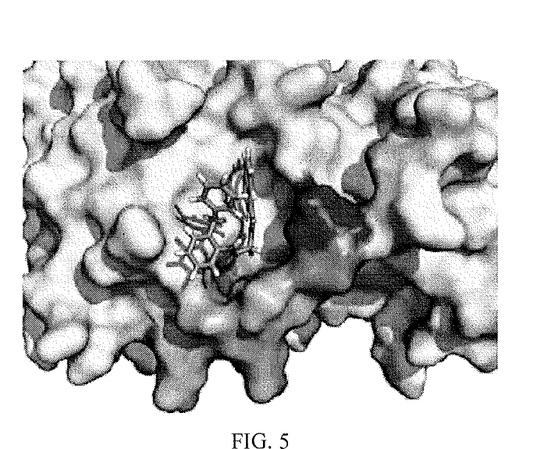
FIG. 5 shows the result of an Energy Minimization of the interaction of AOH39 with the PIP Box Domain of caPCNA.

FIG. 5 shows the result of an Energy Minimization of the interaction of AOH39 with the PIP Box Domain of caPCNA. The binding modes of AOH39 were initially built using All-Around Docking (AAD) (Nam S, Wen W, Schroeder A, Herrmann A, Yu H, Cheng X, Merz K H, Eisenbrand G, Li H, Yuan Y C, Jove R, "Dual inhibition of Janus and Src family kinases by novel indirubin derivative blocks constitutively-activated Stat3 signaling associated with apoptosis of human pancreatic cancer cells", Mol. Oncol. 2013 June; 7(3):369-78. doi: 10.1016/j.molonc.2012.10.013 PMID: 23206899) and refined by Metadynamics (Laio, A.; Parrinello, M. (2002). "Escaping free-energy minima". Proceedings of the National Academy of Sciences of the United States of America 99 (20): 12562-12566.) at 50 ns simulation. The binding affinity of AOH39 to caPCNA is predicted to be −4.62 kcal/mol using Schrödinger Glide Docking software at XP precision.

Growth Inhibition Analysis of AOH 39 in Cancer Cells.

Figure 6:
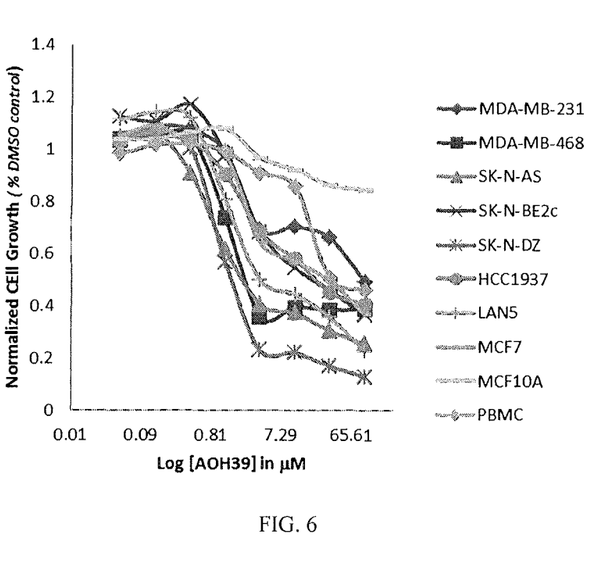
FIG. 6 shows the effect of AOH39 on the proliferation of cancer and non-cancer cell lines.

The effect of AOH39 on the proliferation of cancer and non-cancer cell lines was studied, with the results summarized in FIG. 6. Viability of Breast Cancer and Neuroblastoma cell lines incubated with AOH39 or a DMSO control lacking drug. Proliferation was monitored using the CellTiter Glo Assay (Promega Inc., Madison, Wis.) (https://www.promega.com/products/cell-health-and-metabolism/cell-viability-assays/celltiter-glo-luminescent-cell-viability-assay/). The X-axis is the log value of AOH39 concentration in uM, where 0 corresponds to 1 uM and 1 corresponds to 10 uM. The graphs were generated using Prism 6. MDA-MB231 and MDA-MB468 are ER− breast cancer cell lines; SK-N-AS, SK-N-BE2c, SK-N-DZ lines are neuroblastoma cell lines; LAN5 cells—neuroblastoma bone met; HCC1937 is a BRCA1 defective Breast Cancer cell line; MCF7 is an ER+ breast cancer cell line; MCF10A is a non-malignant but immortalized breast cell line; PBMC—peripheral blood monocytes (proliferating normal cells). The X-axis is plotted as the log of the AOH39 concentration, where 1.0 corresponds to 10 uM. The Y-Axis shows cell proliferation as a percentage of proliferation in PBS/DMSO without added AOH39.

Effect of AOH39 on the Viability of Pancreatic Cancer Cell Lines

Figure 7:
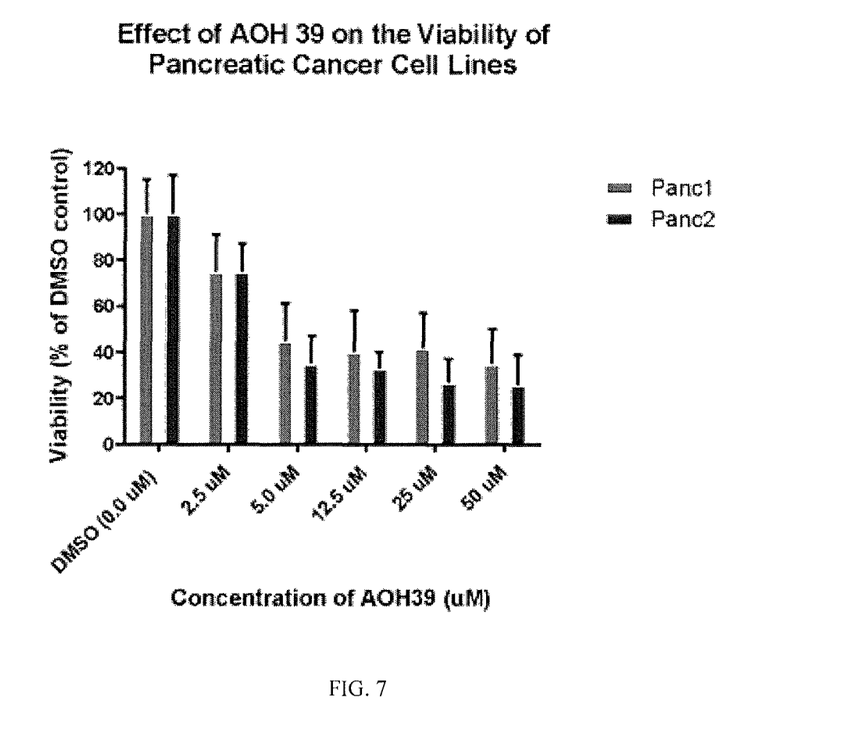
FIG. 7 show the effect of AOH39 on the proliferation of pancreatic cancer cell lines.

The effect of AOH39 on the proliferation of pancreatic cancer cell lines is summarized in FIG. 7. Percent viability of the Panc 1 and Panc 2 cell lines incubated with AOH39 at the indicated concentrations relative to PBS/DMSO (without drug) is plotted on the Y-axis, and the X-axis shows the AOH39 concentration in uM. Proliferation was monitored using the CellTiter Glo Assay (Promega Inc., Madison, Wis.). (https://www.promega.com/products/cell-health-and-metabolism/cell-viability-assays/celltiter-glo-luminescent-cell-viability-assay/). The graph was generated using Prism 6.

Effect of AOH39 on Cell Viability in a Variety of Malignant and Non-malignant Cell Lines.

Figure 8:
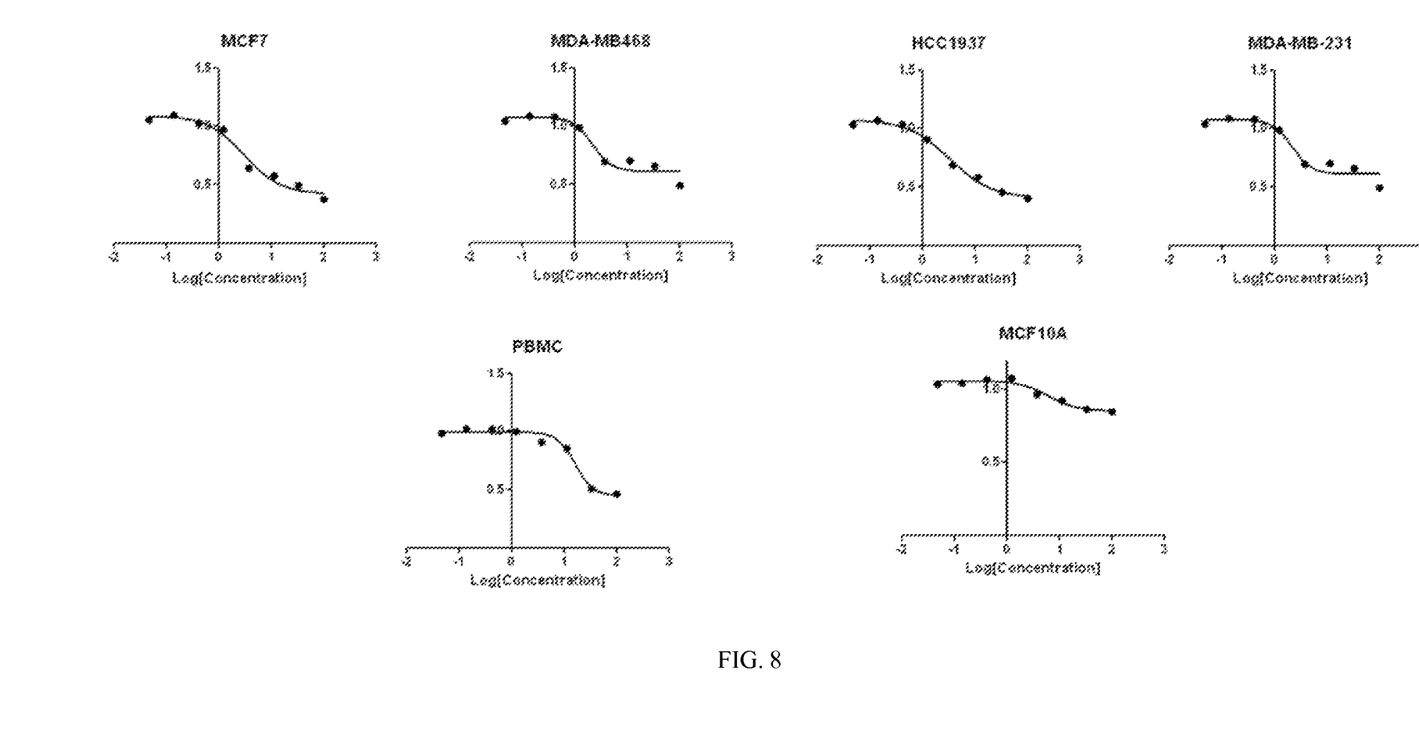
FIG. 8 shows the effect of AOH39 on cell viability in a variety of malignant and non-malignant breast cell lines.
Figure 9:
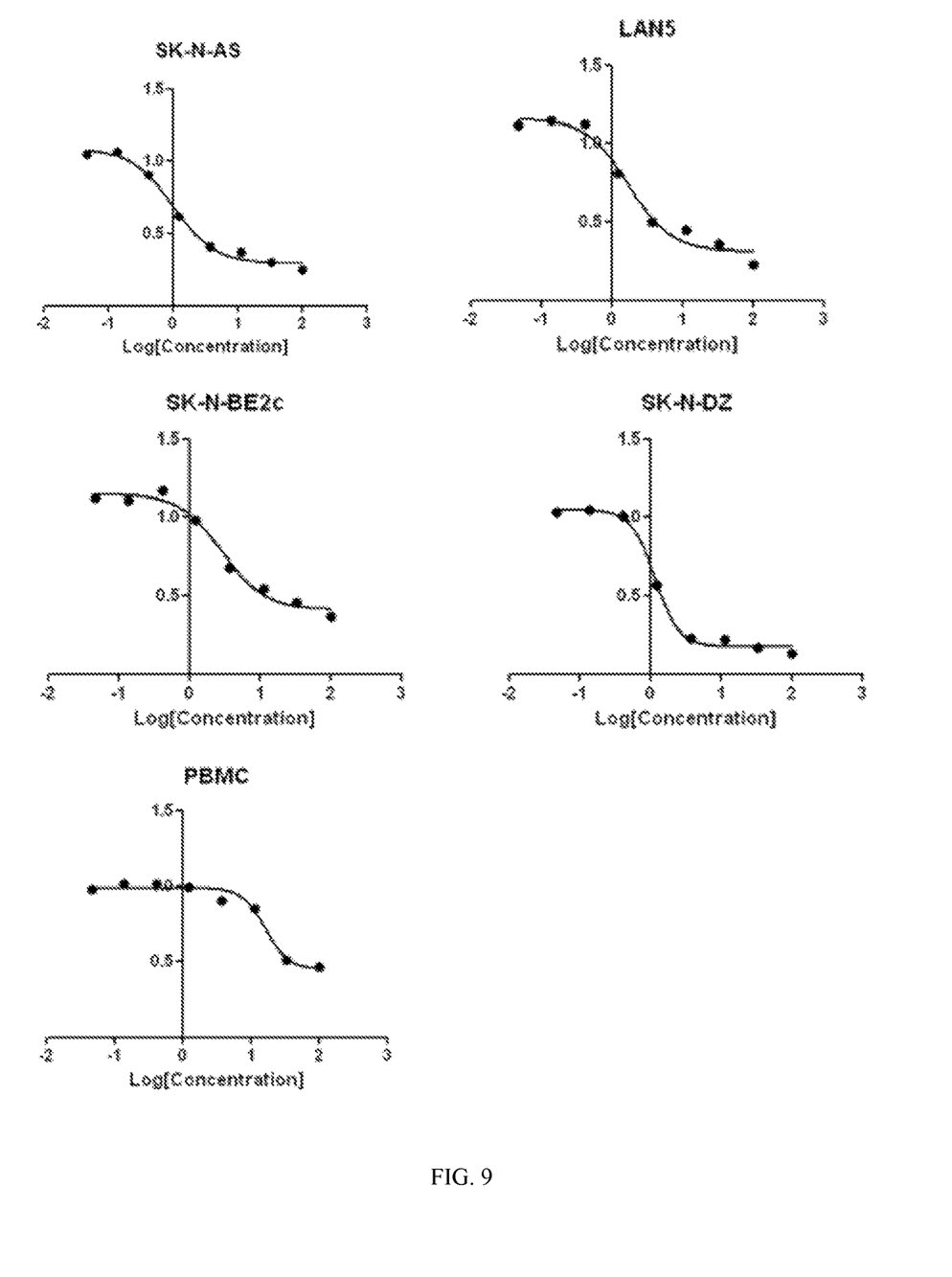
FIG. 9 shows the effect of AOH39 on cell viability in neuroblastoma cell lines and peripheral blood monocytes.

Effect of AOH39 on cell viability in a variety of malignant and non-malignant cell lines is shown in Table 1, and in FIGS. 8 and 9.

TABLE 1

| Cell line | Effect of AOH39 on Cell Viability IC$_{50}$ (μM) |
|---|---|
| PBMC | 13.2 |
| MCF10A | 6.2 |
| MCF7 | 3.1 |
| HCC1937 | 2.2 |
| MDA-MB468 | 3.3 |
| MDA-MB231 | 1.0 |
| SK-N-AS | 2.2 |
| SK-N-BE2c | 2.9 |
| SK-N-DZ | 1.7 |
| LAN5 | 1.2 |

The IC50's listed in Table 1 and in FIGS. 8 and 9 were determined by monitoring cell proliferation in the absence or presence of increasing concentrations of AOH39 using the Cell-Titer Glo Assay, (Promega Inc., Madison, Wis.) which monitors the energy status of the entire culture and the viability of the cell population. (https://www.promega.com/products/cell-health-and-metabolismicell-viability-assaysi-celltiter_glo-luminescent-cell-viability-assay/). As the population doubles so does the quantum yield from the assay. HCC1937 is a BRCA1 defective Breast Cancer cell line; MCF7 is an ER+ breast cancer cell line; MDA-MB231 and MDA-MB468 are ER-aggressive breast cancer cell lines. SK-N-AS, SK-N-BE2c, SK-N-DZ lines are neuroblastoma cell lines and LAN5 cells are a cell line derived from a neuroblastoma bone metastasis; MCF10A is a non-malignant but immortalized breast cell line. PBMC—peripheral blood monocytes (proliferating normal cells), and MCF10A is an immortalized but non-malignant breast epithelial cell line. Referring to FIGS. 8 and 9, the X-axis is the Log of AOH39 concentration in uM, where 0 corresponds to 1 uM and 1 corresponds to 10 uM. The Y-Axis indicates cell proliferation as a percentage of identical cell cultures grown in PBS/DMSO without added AOH39.

What is claimed is:

1. A method of reducing cellular proliferation of breast cancer, pancreatic cancer, or neuroblastoma cancer cells that express a cancer specific isoform of proliferating cell nuclear antigen (caPCNA) in a patient in need thereof, comprising administering a therapeutically effective amount of a compound of the formula or a pharmaceutically acceptable salt thereof.

2. A method for reducing cellular proliferation of breast cancer, pancreatic cancer, or neuroblastoma cancer cells that express a cancer specific isoform of proliferating cell nuclear antigen (caPCNA) comprising administering a therapeutically effective amount of a compound of the formula or a pharmaceutically acceptable salt thereof.

3. A pharmaceutical composition comprising a compound of the formula or a pharmaceutically acceptable salt thereof, and further comprising one or more carriers, diluents, or excipients.

4. The method of claim 1, wherein administration of said compound augments another chemotherapeutic method.

5. A pharmaceutical composition according to claim 3, further comprising a second chemotherapeutic agent.

* * * * *